US011865220B1

(12) United States Patent
Koester

(10) Patent No.: US 11,865,220 B1
(45) Date of Patent: *Jan. 9, 2024

(54) CLEANING KIT FOR REGIONS IN HEALTH CARE FACILITIES

(71) Applicant: The Tuway American Group, Inc., Troy, MI (US)

(72) Inventor: Douglas Koester, Troy, MI (US)

(73) Assignee: THE TUWAY AMERICAN GROUP, INC, Troy, MI (US)

(*) Notice: Subject to any disclaimer, the term of this patent is extended or adjusted under 35 U.S.C. 154(b) by 216 days.

This patent is subject to a terminal disclaimer.

(21) Appl. No.: 17/135,827

(22) Filed: Dec. 28, 2020

Related U.S. Application Data

(62) Division of application No. 15/945,507, filed on Apr. 4, 2018, now Pat. No. 10,874,757.

(60) Provisional application No. 62/481,651, filed on Apr. 4, 2017.

(51) Int. Cl.
*A61L 2/232* (2006.01)
*B65D 75/30* (2006.01)
*A47L 13/17* (2006.01)

(52) U.S. Cl.
CPC .............. *A61L 2/232* (2013.01); *B65D 75/30* (2013.01); *A47L 13/17* (2013.01)

(58) Field of Classification Search
CPC .......... A61L 2/232; B65D 75/30; A47L 13/17
See application file for complete search history.

(56) References Cited

U.S. PATENT DOCUMENTS

| 5,639,532 | A | 6/1997 | Wells |
| 10,874,757 | B1* | 12/2020 | Koester ................... A61L 2/232 |
| 2008/0149526 | A1 | 6/2008 | Sivakumar et al. |
| 2013/0061414 | A1 | 3/2013 | Swist et al. |
| 2015/0208892 | A1 | 7/2015 | Policicchio et al. |
| 2015/0265126 | A1 | 9/2015 | Brown et al. |
| 2018/0056337 | A1 | 3/2018 | Pelletier |
| 2019/0023477 | A1 | 1/2019 | Kelley et al. |

* cited by examiner

*Primary Examiner* — Alexander Markoff
(74) *Attorney, Agent, or Firm* — Young Basile Hanlon & MacFarlane, P.C.

(57) ABSTRACT

A cleaning and sanitizing kit for use in a defined region of a hospital and a method employing the same.

18 Claims, 12 Drawing Sheets

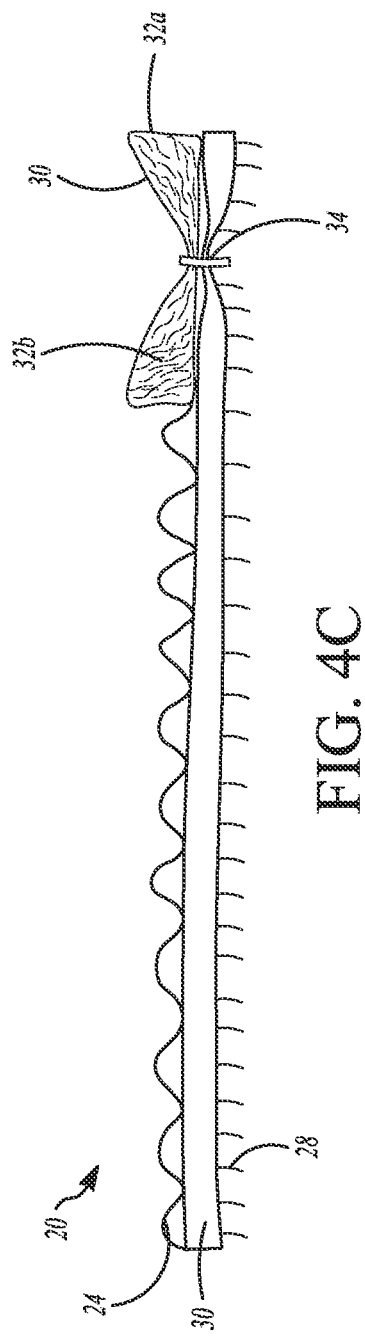
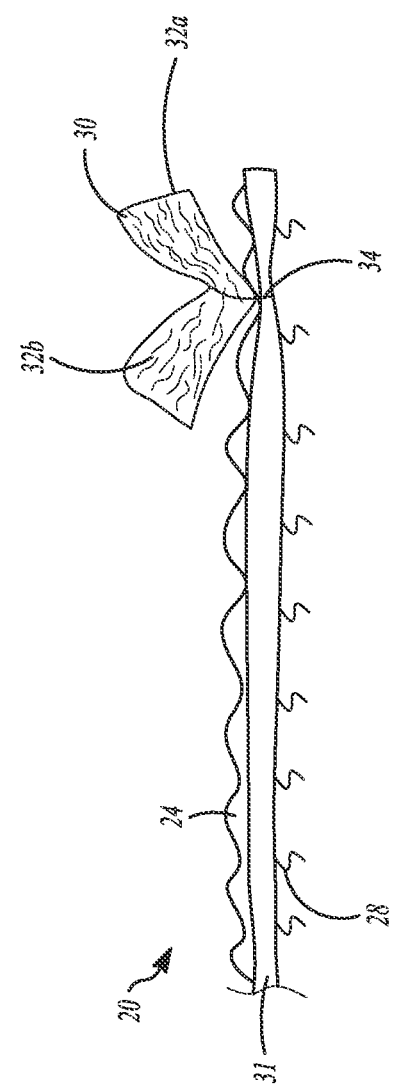

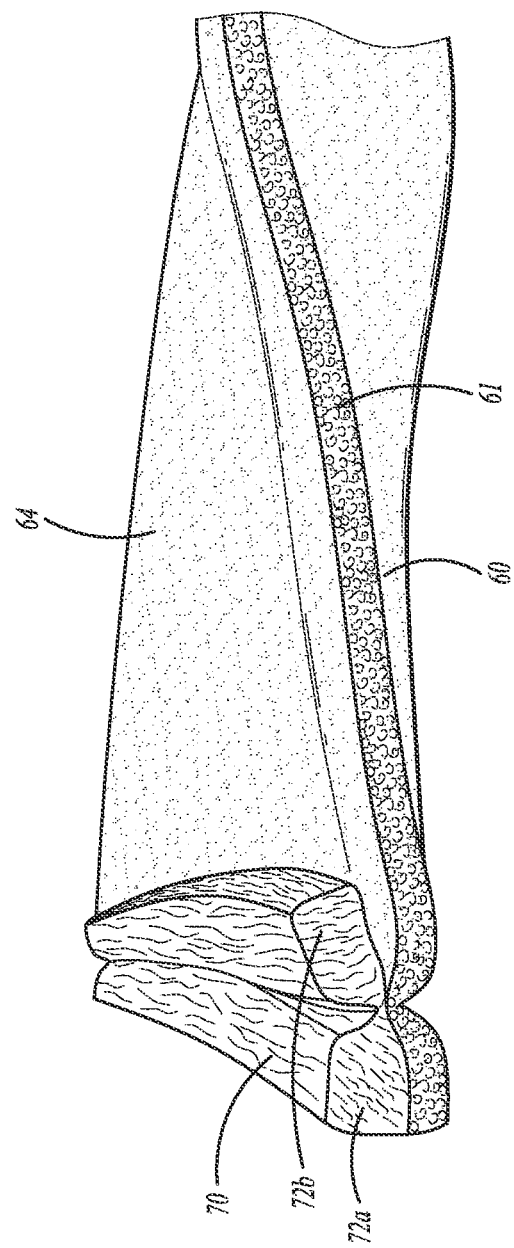

CLEANING KIT FOR REGIONS IN HEALTH CARE FACILITIES

The present application is a divisional application of U.S. application Ser. No. 15/945,507 filed Apr. 4, 2018, currently pending which claims priority to U.S. Provisional Application Ser. No. 62/481,651 filed Apr. 4, 2017, the specifications of which are incorporated by reference herein in entirety.

TECHNICAL FIELD

This disclosure relates to methods and devices for accomplishing and facilitating one or more cleaning operations in health care facilities. More particularly, the present disclosure relates to methods and devices for accomplishing defined cleaning operations in isolated discrete regions in a health care setting.

BACKGROUND

The need to maintain clean and sanitary conditions in health care environments is an important factor in the delivery of efficient and effective health care to individuals and to the community at large. Maintaining high standards of cleanliness and sanitation is also important for the safety of the patients, hospital employees and those who are either directly or indirectly in contact with those facilities.

In order to promote health and safety, vigilant attention must be directed to areas were the risk of infection and contamination is greatest. In many instances, these areas include locations such operating rooms, intensive care rooms, emergency room facilities, isolation rooms and the like. Studies have found that careful attention to cleaning and sanitization of these areas can reduce proliferation of hospital-borne pathogens and can reduce the number of hospital-acquired infections and diseases. This is particularly true in high-use areas such as operating rooms and in areas such as intensive care rooms. Frequent and thorough cleaning and sanitation reduces such risks markedly.

Such efforts can be compromised by the speed at which the sanitization and cleaning operations must occur. In hospital operating rooms, the interval in which the area can be cleaned and sanitized may be as short as eight to ten minutes during peak usage time. Thus, it is important the all necessary cleaning and sanitizing equipment be readily available to ensure that the proper cleaning operations can be accomplished quickly and effectively.

Cleaning operations can also be a source of cross contamination between various operating rooms or the like if proper clearing procedures are not observed as when a cleaning implement is across multiple hospital areas such as operating rooms. Thus, it would be desirable to provide a cleaning kit and method that could be brought to the hospital area to be cleaned, provide for systematic thorough cleaning and can be removed from the newly cleaned area in a safe and complete manner. It is also desirable that any elements of the cleaning unit can be readily identifiable and, where desired, can be biodegradable or at least partially biodegradable.

SUMMARY

Disclosed herein is a cleaning and sanitizing kit for use in a defined region of a hospital and a method employing the same. The cleaning and sanitizing kit includes an outer bag member, the outer bag member composed of a polymeric film material, the outer bag member defining a sealed inner chamber. The kit also includes a plurality of non-woven wipe sheets contained in the sealed inner chamber of the outer bag as well as at least two single-use vertical surface washing pads contained in the sealed inner chamber of the outer bag that includes at least one visible indicia present thereon. At least one single-use mop head bundle is also contained in the sealed inner chamber of the outer bag, the mop head bundle has a plurality of elongated strip members and a headband, the elongated strip members connected to the headband and projecting outward therefrom in spaced parallel relationship to one another, the parallel strip members composed of non-woven fabric material with the headband configured to contact a mop connector member. The kit also includes at least two single-use floor mop pads contained in the sealed inner chamber of the outer bag in which each respective single-use floor mop pad having opposed first and second elongated surfaces, wherein the first elongated surface comprises a compressible microfiber region and wherein the opposed second region has loop pile surface region configured to releasably contact a pad head and at least one scrubbing member projecting from the microfiber region, wherein each single-use floor pad has at least one color indicia associated therewith. The kit also includes at least one sealable disposable biohazard bags located folded relationship in the sealed inner chamber, each disposable biohazard bag composed of a polymeric film having a thickness between 0.5 mil and 10.0 mil.

Also disclosed is a method for cleaning and sanitizing a discrete treatment region that includes the steps of introducing the cleaning kit as disclosed into the discrete treatment region to be cleaned. Once the kit is introduced in the discrete treatment region, opening sealed inner chamber of the outer bag member and transferring the plurality of nonwoven wipe sheets in a folded state from the outer bag member to a measured volume of a first sanitizing solution; transferring the at least two single-use vertical surface washing pads from the outer bag member to a measured volume of a sanitizing solution; transferring at least one of the least two single-use floor mop pads from the outer bag member to a measured volume of a third sanitizing solution, the measured volume of a sanitizing solution sufficient to be absorbed by the at least two single-use vertical surface washing pads and contacting the respective surface with the associated use-appropriate pad. After contact, sequentially transferring the use-appropriate pad into the sealable disposable biohazard bag. Upon completion of sanitizing operations in the discrete treatment regions transferring all kit elements into the biohazard bag and closing the bag for disposal.

These and other aspects of the present disclosure are disclosed in the following detailed description of the embodiments, the appended claims and the accompanying figures.

BRIEF DESCRIPTION OF THE DRAWING

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 4C is a cross-sectional view of the vertical surface washing pad of FIG. 4A taken along the 4C line of FIG. 4A;

FIG. 4D is a detail cross sectional view of the agitator region of the vertical surface washing pad of FIG. 4A;

FIG. 6C is a detail side view of lateral end of the single use floor pad of FIG. 6A;

DETAILED DESCRIPTION

Figure 1:
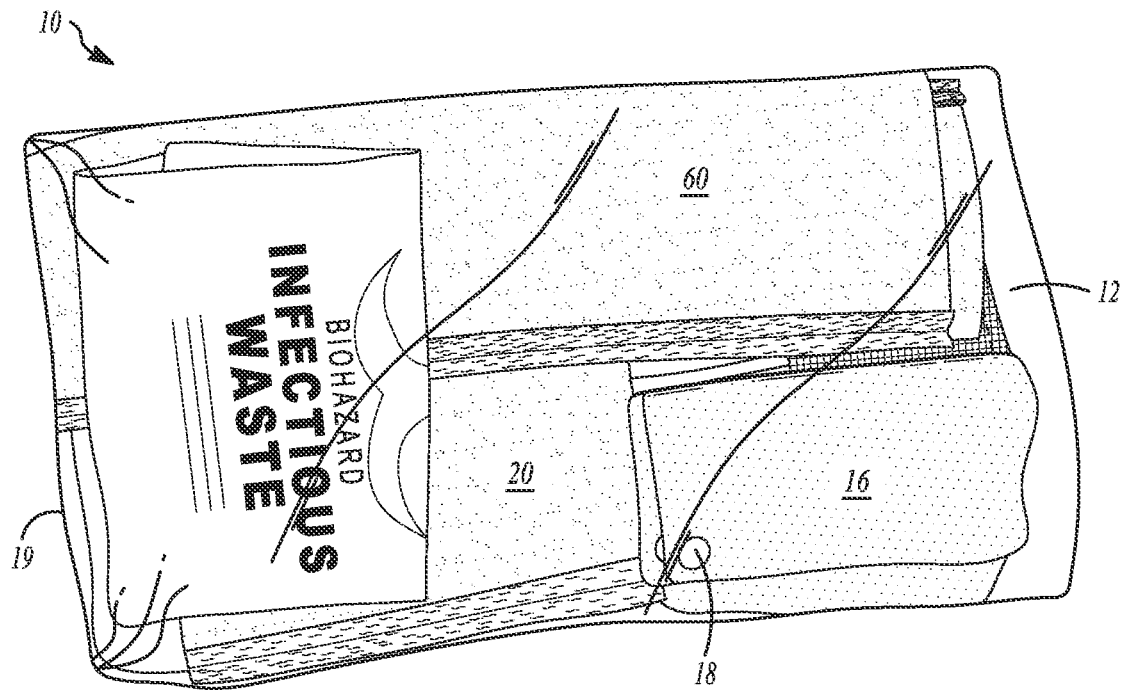
FIG. 1 is top plan view of an embodiment of the kit as disclosed herein.

The present disclosure is directed to a process and kit for cleaning and/or sanitizing a discrete region in a healthcare facility. Cleaning and/or sanitizing is an important function in maintaining the healthful environment in healthcare facilities such as hospitals, rehabilitation facilities nursing care facilities and the like. The present method and kit can be employed to execute and/or augment cleaning and/or sanitizing operations a discrete treatment region in a healthcare facility. As used herein, the term "discrete treatment region" can include a location such as an operating room or theater, post-operative recovery room, a patient room as would be found in intensive care units, post-operative treatment units, etc. The kit 10 as disclosed herein is configured to be delivered to an individual discrete treatment region to provide the disposable cleaning materials required to affect the required cleaning and sanitation operation and to provide for a safe and effective disposal of soiled or used cleaning products.

The kit 10 as disclosed herein includes a sealed outer bag member 12 that defines an interior chamber 14. The chamber 14 is configured to have a sufficient interior volume to maintain the articles defined herein in fixed relationship to one another. In certain embodiments, it is contemplated that the articles contained in the chamber 14 defined in the bag member 12 will be oriented in a use-specific manner such that the order of removal conforms with the cleaning process to which the container articles are employed.

The outer bag member 12 can be made of a suitable polymeric material having a thickness sufficient provide structural integrity to the bag member 12 but to permit ready opening and access to the interior contents when the bag member 12 is in a sealed condition. In certain embodiments, the bag member 12 can be composed of polymeric material in suitable thickness so as to isolate the materials held therein from the outer environment until the bag member is opened. In the embodiment depicted in the drawing figures, the polymeric material can be transparent or semi-transparent. Non-limiting examples of suitable polymeric material include polyethylene, polypropylene and the like such as high-density polyethylene (HDPE), low-density polyethylene (LDPE), or linear low-density polyethylene (LLDPE) and the like. In certain embodiments, the polymeric material employed in the bat member 12 can have a thickness between The material of construction can be oriented or non-oriented as desired or required. The polymeric material employed in the outer bag member 12 can have a thickness between 0.5 mil and 10 mil in certain embodiments. The polymeric material can between 1 mil and 5 mil in certain embodiments. The outer bag member can be configured as a two-layer poly bag and the respective layers can joined to one another at the respective edges by heat sealing, adhesive sealing or the like.

Where desired or required, the outer bag member 12 and articles contained therein can be sealed under suitable standards of cleanliness such as those which may be mandated by a suitable health care setting and/or by various governmental and/or industry regulatory agencies. Thus, where desired or required, the articles present in the outer bag member 12 can be assembled under standards such as "clean", "sanitary", "aseptic" or the like.

The kit 10 can include specific one-time use items in number quantity and configuration that are assembled in the outer bag member 12 for the cleaning operation required for the specific location in the health care facility. In addition to such use-specific articles, the kit 10 as disclosed herein includes a plurality of non-woven wipe sheets 16. In the embodiment depicted in the drawing figures, the non-woven wipe sheets 16 are contained in the sealed interior chamber 14 defined by the outer bag member 12 at a location proximate to an opening member 17. The opening member 17 can be present in the seam between the respective plastic sheets or can be configured as a tear strip or the like proximate to a leading edge 19 of outer bag member 12.

Figure 2:
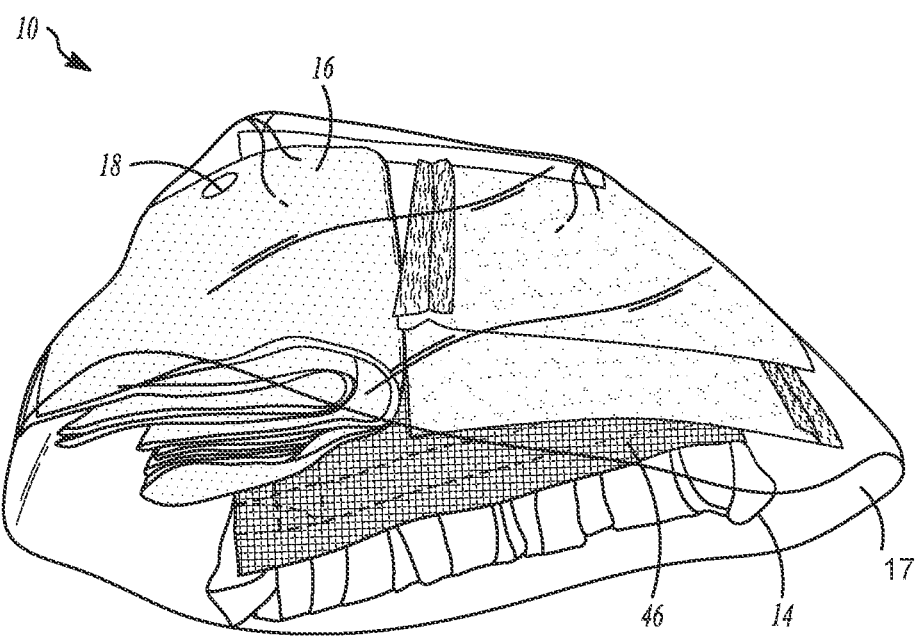
FIG. 2 is side view of the kit of FIG. 1.
Figure 3A:
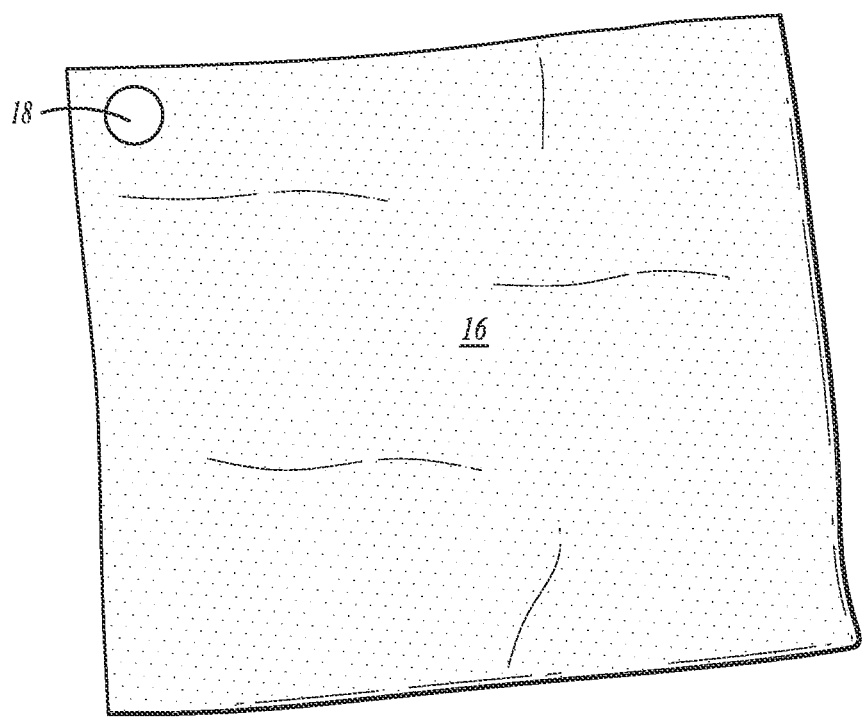
FIGS. 3A and 3B are detail top views of an embodiment of the non-woven wipe sheet of the kit of FIG. 1 in the folded and unfolded states.
Figure 3B:
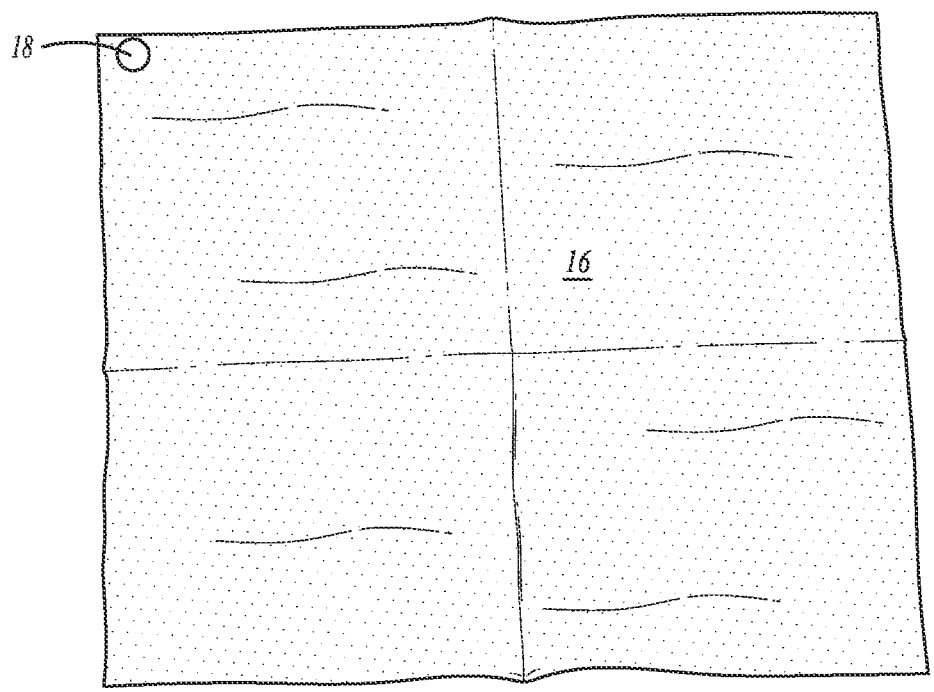
Figure 4B:
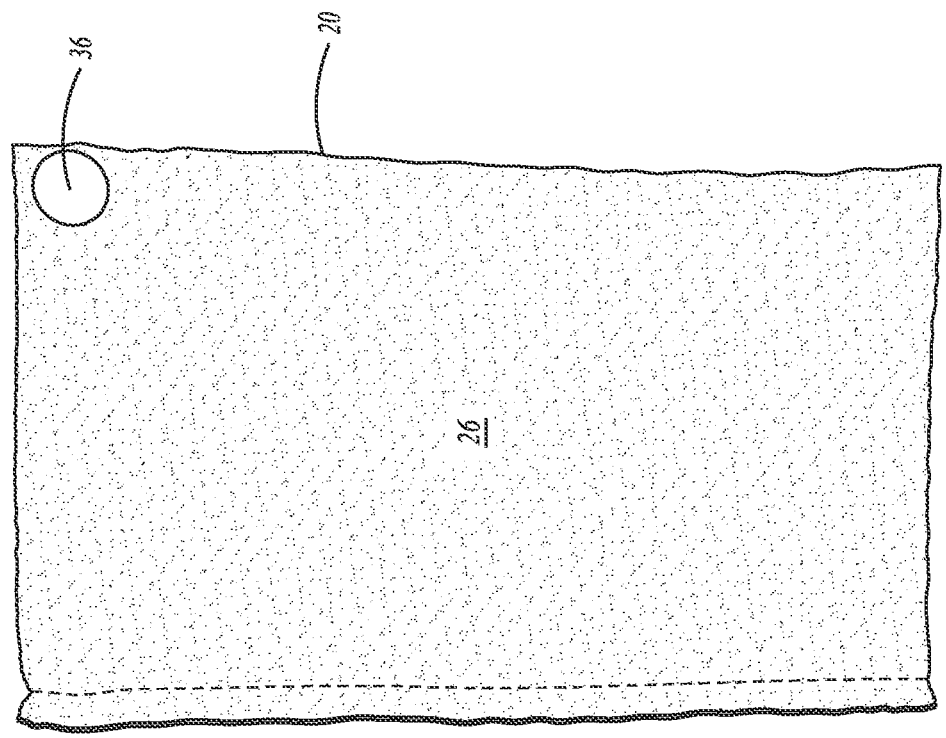
FIG. 4B is the bottom or devise contact surface view of the vertical surface washing pad of FIG. 4A.
Figure 4A:
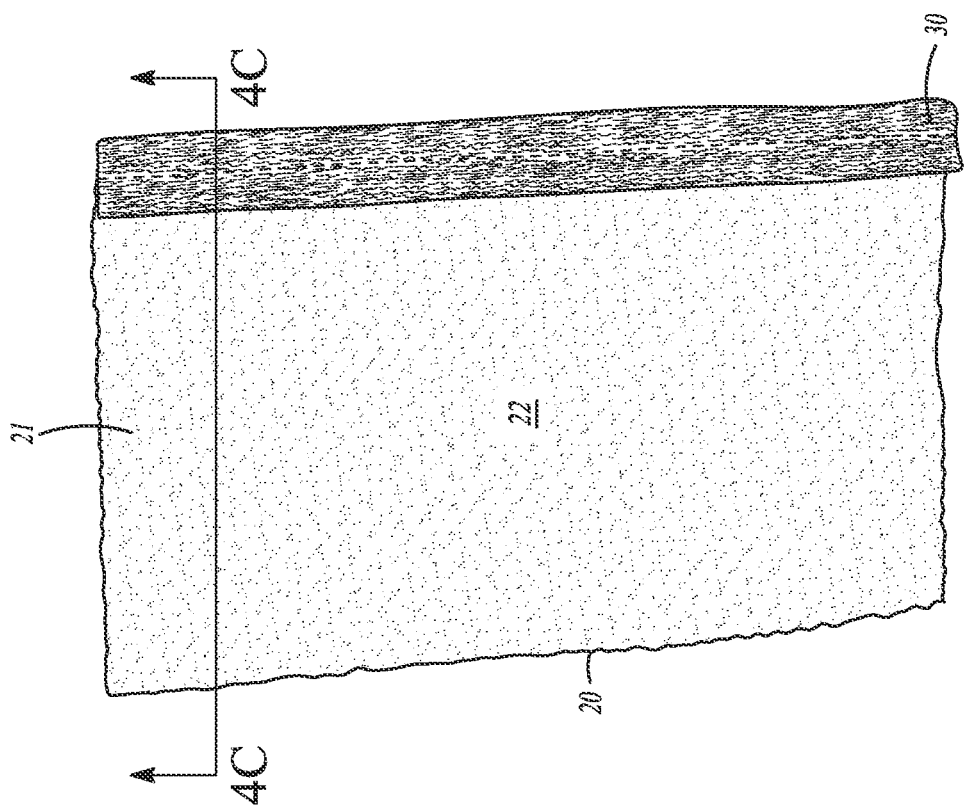
FIG. 4A is a top or washing surface view of an embodiment of the vertical surface washing pad of the kit of FIG. 1.
Figure 5A:
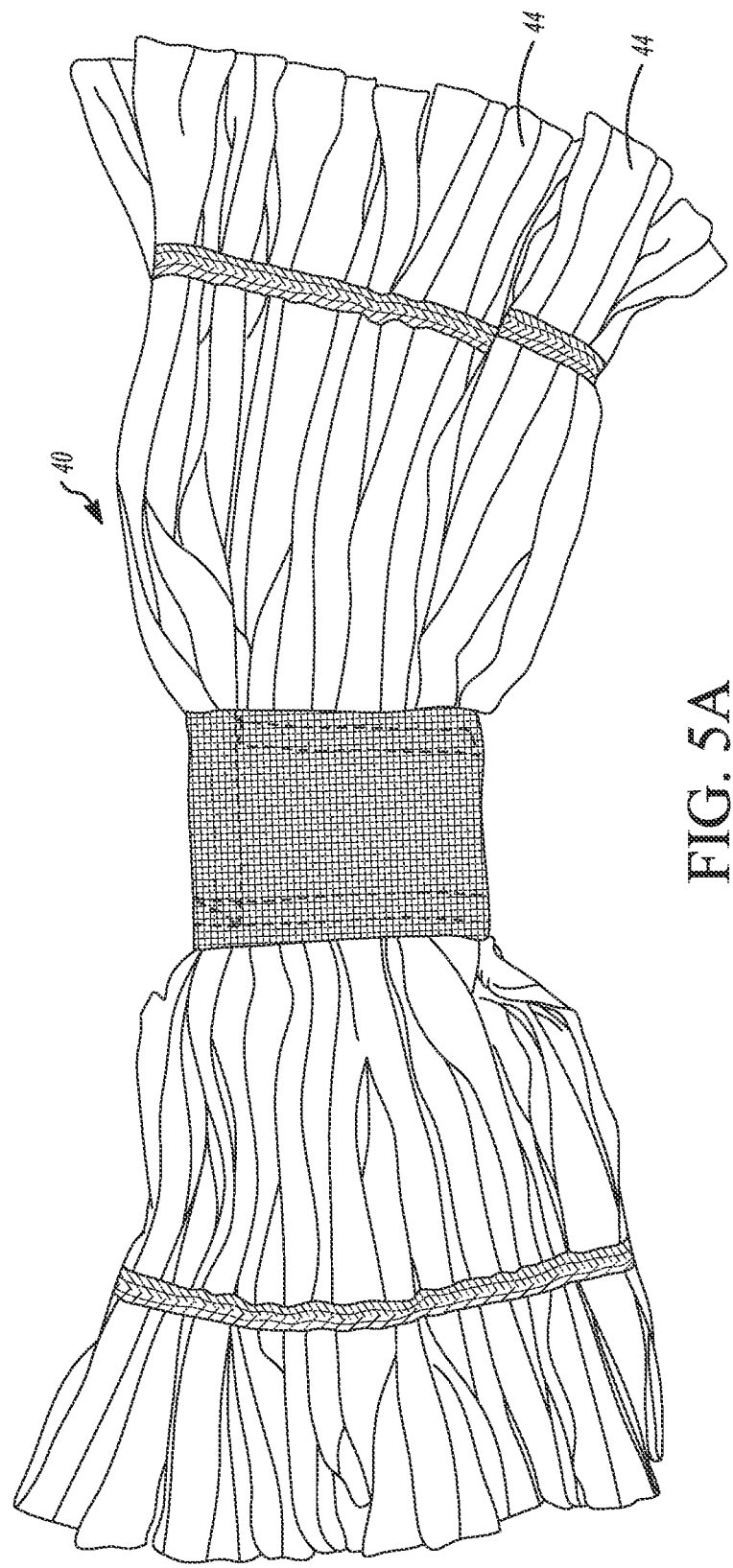
FIGS. 5A, 5B and 5C are detail views of an embodiment of the mop head bundle of the kit of FIG. 1.
Figure 5B:
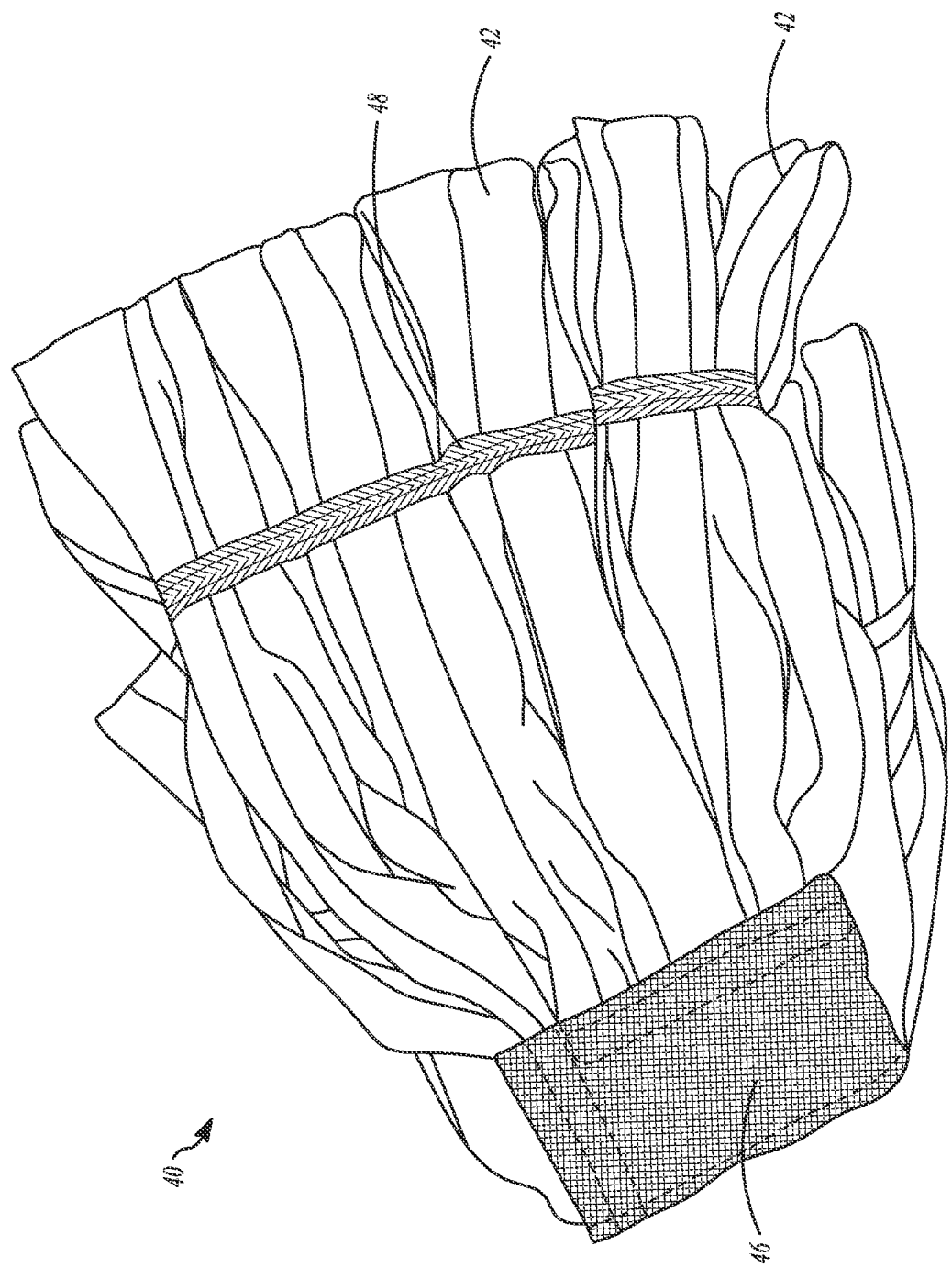
Figure 5C:
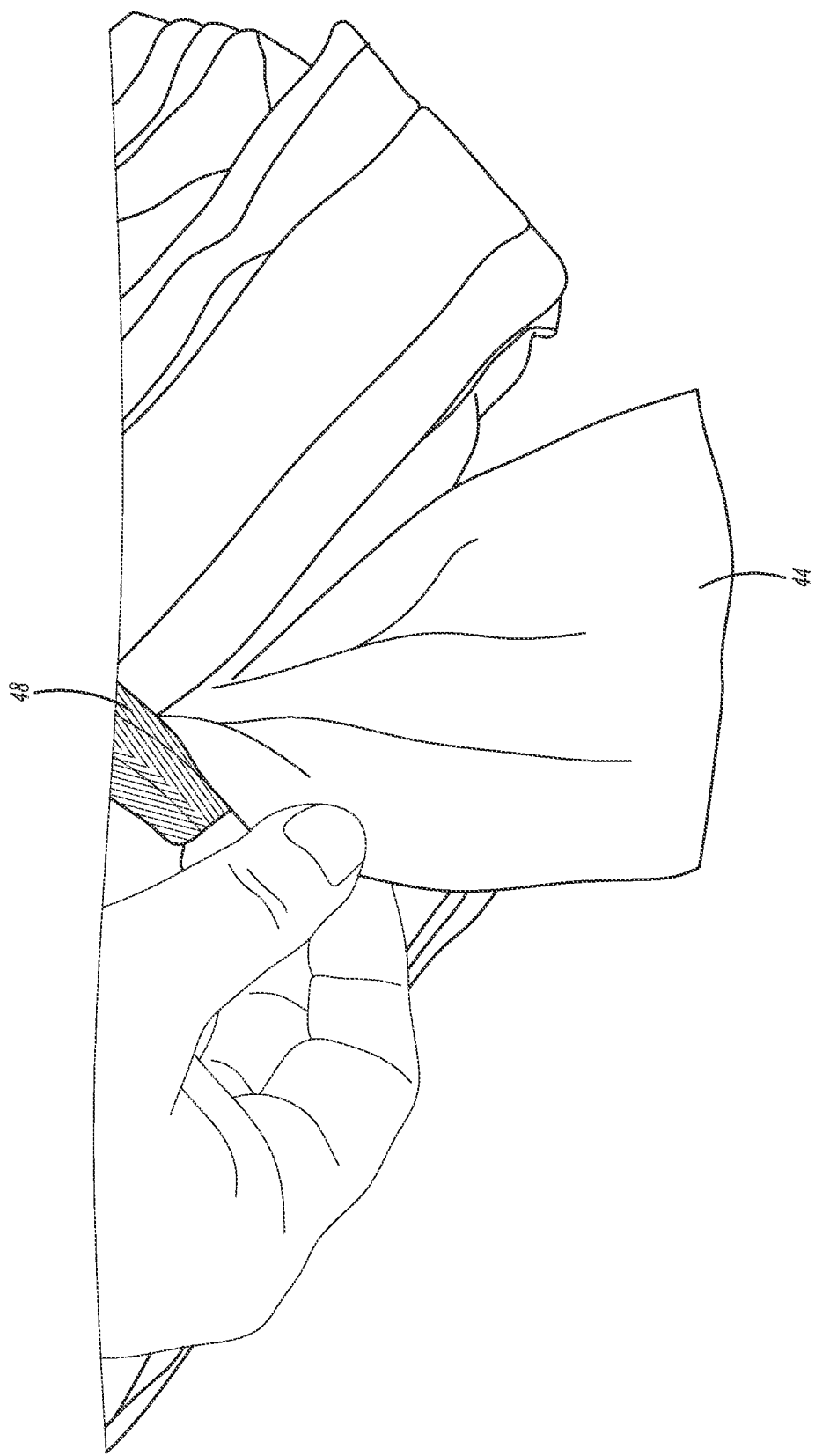
Figure 6A:
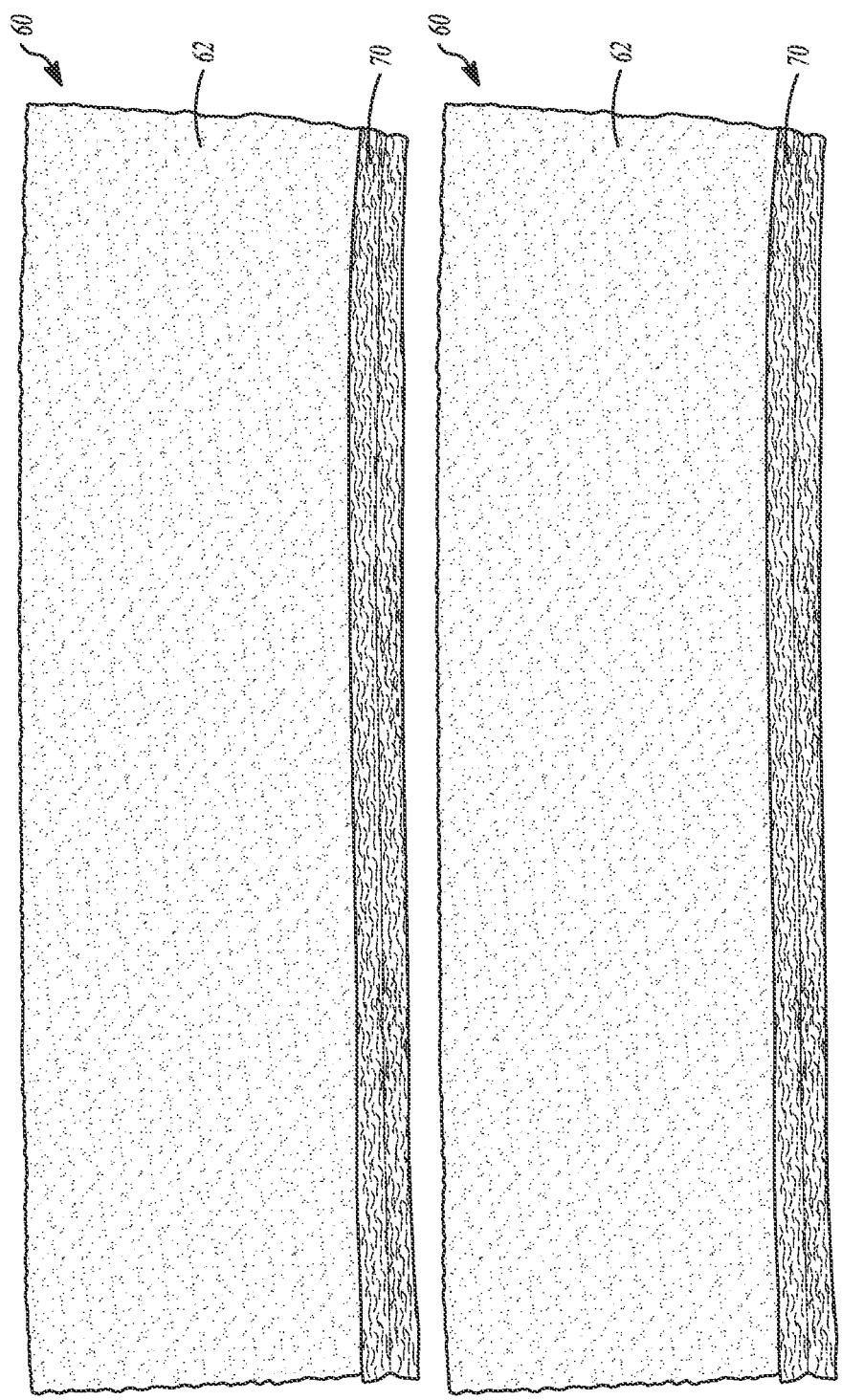
FIG. 6A is a top plan view of an embodiment of single use floor pad of the kit of FIG. 1.
Figure 6B:
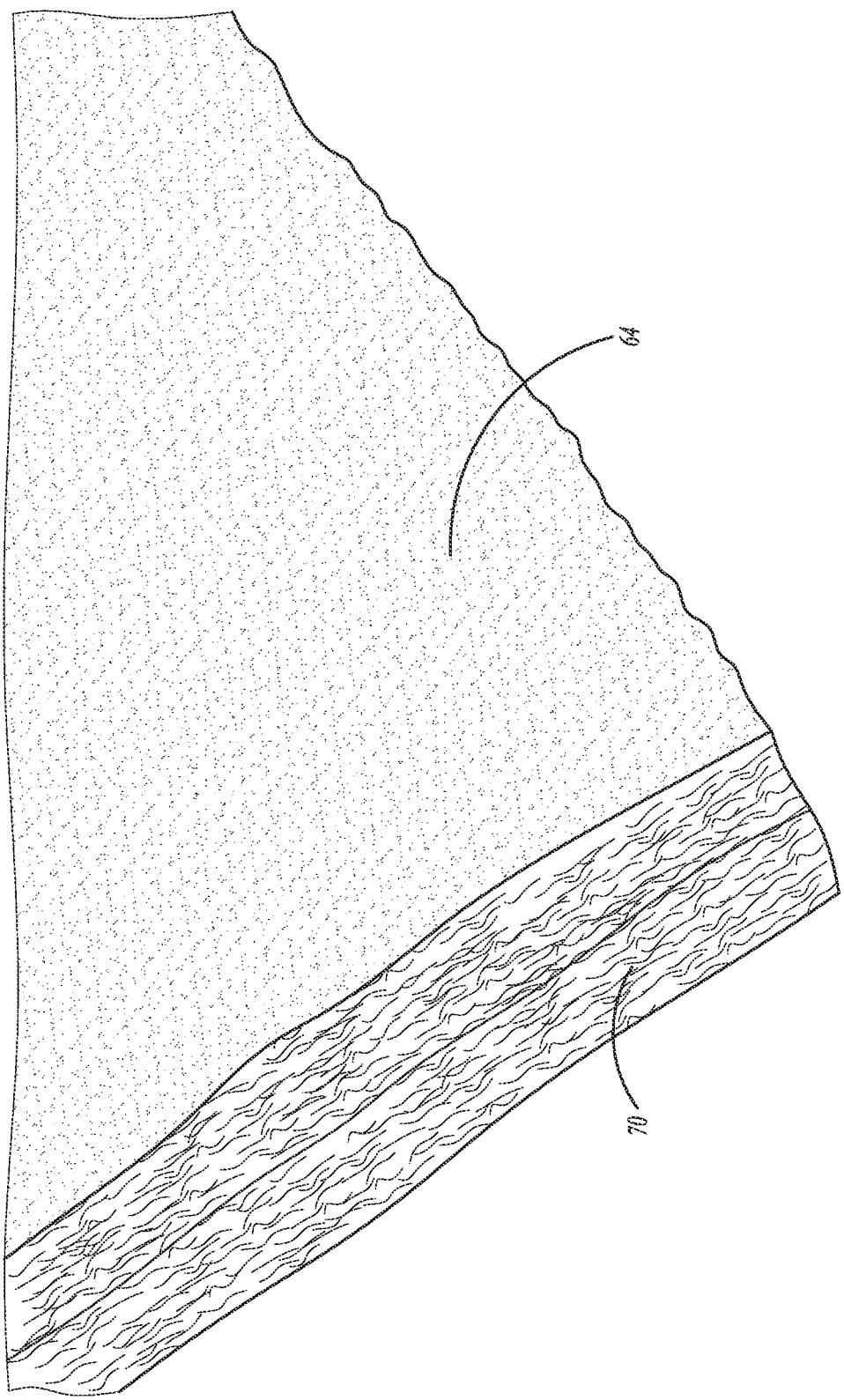
FIG. 6B is a detail view of the single use floor pad of FIG. 6A.
Figure 6D:
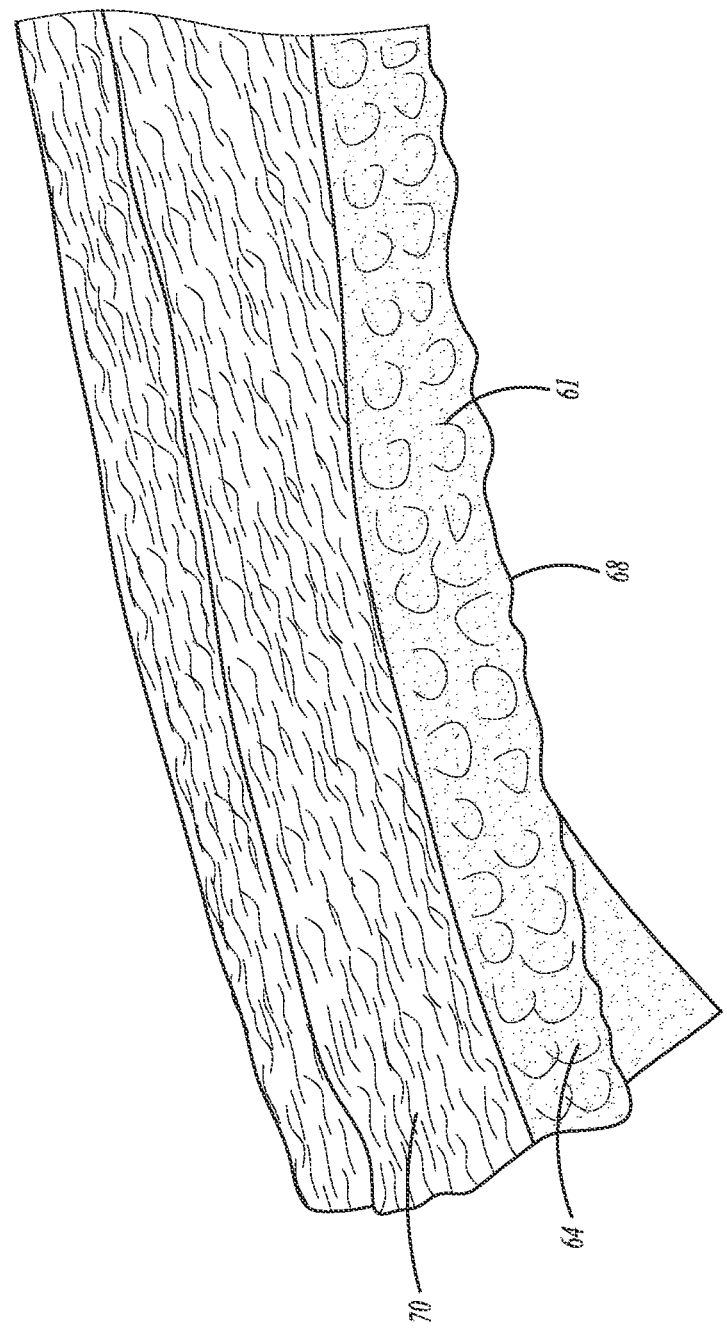
FIG. 6D is a detail side view of an elongate edge of the single use floor pad of FIG. 6A.
Figure 7:
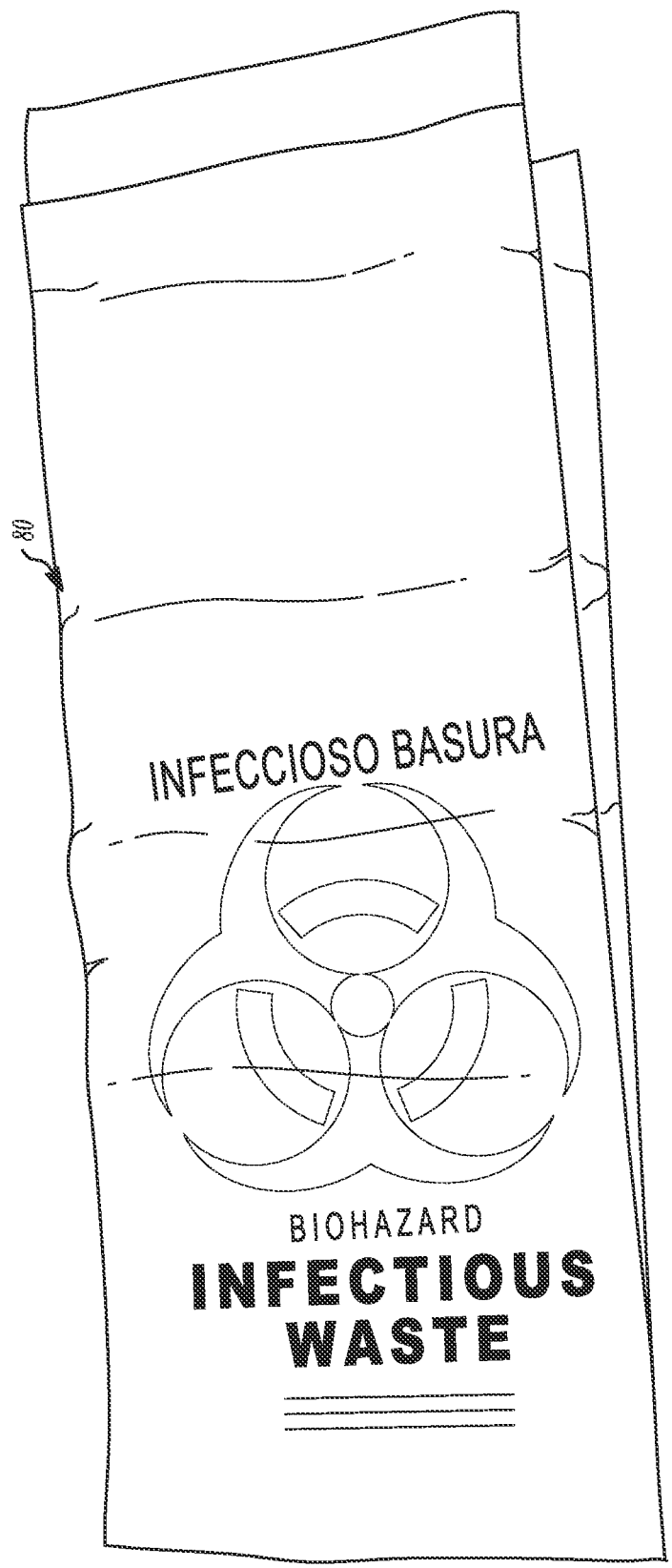
FIG. 7 is a detail view of an embodiment of the disposable biohazard bag of the kit FIG. 1 in a partially folded orientation.

In certain embodiments, the kit 10 will include a plurality of non-woven wipe sheets, .in certain embodiments, the kit 10 will contain between 2 and 10 non-woven wipe sheets 16. In the embodiment depicted in FIGS. 1 and 2, the plurality of non-woven wipe sheets 16 are oriented in the top right quadrant of the outer bag member 12 in a bundle configuration to facilitate ready removal of the non-woven wipe sheets at the commencing of cleaning operations. The bundle configuration may include at least one, and possibly, two folds.

The non-woven wipe sheets 16 present in the kit 10 are composed of non-woven fibers which contain one or more of synthetic materials such as polyester, polypropylene and the like, and/or semi-synthetic fibers such as viscose rayon, viscose bamboo and the like. Where desired or required, the synthetic and/or semisynthetic materials can be configured with suitable polymeric or monomeric components to enhance biodegradability and/or facilitate incineration or disposal after use.

In certain embodiments, the non-woven material can be a blend of non-woven fibers present in a ratio between about 1 to 3 and 3 to 1 synthetic to semi-synthetic respectively. In certain embodiments, the synthetic material can be polyester and the semi-synthetic material can be viscose. In some embodiments, the non-wove wipes 16 will contain between 20 to 80% polyester fibers and between 80% and 20% viscose fibers. In certain embodiments, the material can be composed of 50% polyester fibers and 50% viscose fibers.

The individual non-woven wipe sheets 16 can have a thickness between about 0.3 mm and about 1 mm in certain embodiments and can have a weight between 10 and 60 g/square meter. The various unfolded non-woven wipes 16 can have a configuration, surface area, and outer dimensions suitable to facilitate wipe down of elements such as walls, equipment and the like in the specific health care setting to be cleaned. In the embodiment depicted in FIGS. 1 and 2, the non-woven wipe 16 can have a length between 20 cm and 60 cm. In certain embodiments the non-woven wipes 16 can be can be rectangular and can have outer lengths between 35 and 45 cm. In the kit 10, the non-woven wipes 16 can each be present in folded relationship. In the embodiment depicted in the drawing figures, the non-woven wipes 16 can be folded lengthwise laterally twice such that each non-woven wipe 16 is present in the outer bag member 12 in a four-layer thickness with the individual non-woven wipes 16 in stacked relationship to one another. Without being bound to any theory, it is believed that the folded configuration as disclosed herein facilitates removal of the bundle of non-woven wipes 16 from the outer bag member 12 and ultimate separation for end use.

The non-woven wipes 16 each can include at least one indicia or marking such as indicia 18 imparted thereon by printing, weaving or the like. The indicia 18 can be a line, geometric shape or the like. In the embodiment depicted, the indicia 18 is a circle visibly oriented in a corner of each individual rectangular non-woven wipe 16 that can be color-coded to correspond to the various other articles present in the kit 10. It is contemplated that the color-coding can be user specific where desired or required and can correspond to factors such as the degree of biological contamination or hazard possible in the specific area of the hospital or health care facility to be cleaned and/or the manner in which the used non-woven wipes 16 (and other articles) present in the kit 10 are to be handled and treated upon disposal.

It is also considered within the purview of this disclosure that non-woven wipes 16 include additional indicia to inform the user as to the specific area to be cleaned by a specific wipe 16 where desired or required.

The non-woven wipes 16 are configured to be single-use and can have at least one contact surface and be dimensioned to deliver a volume of a material such as a sanitizing charge solution to an accessory surface present in the defined region of a hospital to be cleaned. In the kit 10 as disclosed herein, the non-woven wipes 16 are configured to deliver a predetermined volume of sanitizing and/or anti-microbial material to surfaces such as the lights, and appliances present in the discrete treatment region. The sanitizing and/or antimicrobial material can be a solution that is introduced into contact with at least one of the specific non-woven wipes 16 after removal from the outer bag 12.

The kit 10 can also include at least two single-use vertical surface washing pads 20 also contained in the sealed inner chamber 14 of the outer bag member 12. The respective single-use vertical surface washing pads 20 are dimensioned to be removably attached to a suitable planar pad head that can be mounted in pivotal or swivel relation on a wand as desired or required after the respective vertical surface washing pad 20 removal from the outer bag member 12. In certain embodiments, the single-use vertical surface washing pad 20 can have an elongated rectangular configuration have a major axis between 6 and 12 inches and a minor axis between 3 and 9 inches. Each single use vertical surface washing pad 20 can have a thickness suitable to absorb and deliver s suitable cleaning/sanitizing solution to the vertical surface to be treated. In certain embodiments, the single-use vertical surface washing pad 20 can have a thickness between 0.25 inches and 0.5 inches.

In the embodiment disclosed, the single-use vertical surface washing pad 20 can include an elongated body member 21 having a first elongated surface region 22 and a second elongated surface region opposed to the first elongated surface region. The single-use vertical can include an element composed of a microfiber material layer 24 that extends over at least a portion of the elongated surface region 22. In the embodiment depicted in the drawing figures, the microfiber layer extends over the entire face of the elongated surface region 22. The opposed second elongated region 26 can be configured with a suitable engagement region extending over all or a part of the elongated surface region such as loop region 28. A suitable flexible absorbent region 31 can be interposed between the first and second elongated surface regions and can be composed of a suitable absorbent polymeric foam.

The single-use vertical surface washing pad 20 can also include a suitable agitator strip 30 that is connected to one edge of the single-use vertical surface washing pad 20 and projects outward therefrom. In the embodiment depicted, the agitator or scrubbing member 30 projects from the first surface 22 and overlays a portion of the microfiber material layer 24.

The single-use vertical surface washing pads 20 can also include a suitable colored indicia 36 that is similar to that described in relation to the non-woven wipes 16. The kit 10 can include one or more single-use vertical surface washing pads 20. In certain embodiments, the kit 10 can include a between one and four single-use vertical surface washing pads 20. In the embodiment depicted, the kit 10 has two single-use vertical surface washing pads 20.

When present in the sealed chamber 14 of the outer bag member 12, the at least two single-use vertical surface washing pads 20 can be positioned in overlying relationship with one another. In certain embodiments, the agitator strip 30 composed of a first single-use vertical surface washing pad 20 can be oriented in releasable engagement with the outwardly facing surface of the outermost non-woven wipe sheet 16 present in the non-woven wipe sheet bundle. The opposed elongated surface region 26 of the first single-use vertical surface washing pad 20 can be in releasable engagement with the agitator strip of a second single-use vertical surface washing pad 20 present in the stack. In this way, the removal of the at least two single-use vertical surface washing pads 20 from the chamber 14 can be facilitated. Additionally, it is believed that the releasable engagement of the stack of single-use vertical surface washing pads 20 with each other and optionally with the bundle of non-woven wipe sheets 16 can provide structural stability to the kit 10.

The kit 10 also includes at least one single-use mop head bundle 40 that is contained in the sealed inner chamber 14 of the outer bag member 12. In the embodiment depicted in the various drawing figures, the kit 10 includes one single-use mop head bundle 40. The mop head bundle 40 includes a plurality of elongated strip members 42 that are composed of suitable non-woven strips 44. The strips are connected to a suitable headband member 46 and project outward therefrom in parallel relationship to one another. Each elongated strip member 42 can be composed of a single elongated non-woven fabric material that can be present in pleated relationship if desired or required. The non-woven fabric material can be composed of the same or different material as discussed in relation with the non-woven wipe sheets 16. In certain embodiments, the non-woven material employed in the non-woven strips 44 can be mono-axially oriented such that the fabric in the strands can stretch in lateral direction. It is contemplated that the non-woven strips can have suitable absorbency to absorb and retain materials such as blood, bodily fluids and the like.

The non-woven material employed in the elongated strip members 42 can be composed of non-woven fibers which contain one or more of synthetic materials such as polyester, polypropylene and the like, and/or semi-synthetic fibers such as viscose rayon, viscose bamboo and the like. Where desired or required, the synthetic and/or semisynthetic materials can be configured with suitable polymeric or monomeric components to enhance biodegradability and/or facilitate incineration or disposal after use.

In certain embodiments the non-woven material can be a blend of non-woven fibers present in a ratio between about 1 to 3 and 3 to 1 synthetic to semi-synthetic respectively. In certain embodiments, the synthetic material can be polyester and the semi-synthetic material can be viscose. In some embodiments, the non-wove wipes 16 will contain between 20 to 80% polyester fibers and between 80% and 20% viscose fibers. In certain embodiments, the material can be composed of 50% polyester fibers and 50% viscose fibers.

The headband member 46 can be composed of a suitable material of sufficient strength to bind the various elongated strip member 42 and connect to a suitable floor mop wand (not shown) The headband member 46 can be composed of a material having a color that correspond to the indicia 18, 36 present on other components of the kit 10.

In the embodiment depicted in the drawing figures, the single-use mop head bundle 40 can include one or more tail band members 48 that are bound to the elongated strip member 42 at a spaced distance from the headband 46. Where desired or required, the tail band member(s) 48 can be configured with a suitable color to provide identifying indicia as desired or required. In certain embodiments one or more of the materials that make up the single-use mop head bundle 40 can be biodegradable if desired or required. It is contemplated that, in certain embodiments, the at least one single-use mop head bundle 40 may be optionally present in the kit 10 as disclosed herein based on the nature and usage to which the "discrete treatment region" is employed. Thus, in situations where there is little or no opportunity for generation of large volumes bodily fluids such as blood, etc. it is contempered that the kit 10 can be assembled without the mop head bundle 40.

The kit 10 can also include at least two single-use floor pads 60 contained in the sealed inner chamber 14 of the outer bag member 12. Thus, the respective single-use floor pads 60 are dimensioned to be removably attached to a suitable planar mop pad base that can be mounted in pivotal or swivel relation on a wand as desired or required. In certain embodiments, the single-use floor pad 60 can have an elongated rectangular configuration having a major axis between 12 and 20 inches cm, a minor axis between 3 and 9 inches and a thickness between 0.25 inches and 0.5 inches.

The single-use floor pad 20 can include a first elongated surface region 62 composed of a microfiber material layer that extends over at least a portion of the elongated surface region 62. In the embodiment depicted in the drawing figures, the microfiber layer extends over the entire face of the elongated surface region 62. The opposed second elongated region 66 can be configured with a suitable engagement region extending over all or a part of the elongated surface region such as loop region 68. A suitable flexible absorbent region 61 can be interposed between the first and second surfaces and can be composed of a suitable absorbent polymeric foam.

The single-use floor pad 60 can also include a suitable agitator or scrubbing strip member 70 that is connected to one edge of the single-use floor pad 60 and projects outward therefrom. In the embodiment depicted, the agitator or scrubbing strip member 70 projects from the first surface 62 and overlays a portion of the microfiber material layer 64.

The single-use floor pads 60 can also include a suitable color indicia 66 that is similar to that described in relation to the non-woven wipes 16. The kit 10 can include one or more single-use floor pads 60. In certain embodiments, the kit 10 can include a between one and four single-use floor pads 60. In the embodiment depicted, the kit 10 has two single-use floor pads 60.

In various embodiments, the kit 10 will also include at least one sealable disposable biohazard bag 80 that is located in folded relationship in the sealed inner chamber 14 in the outer bag member 12. In certain embodiments, the kit 10 can include multiple biohazard bags 80 if desired or required. The biohazard bag(s) 80 can have a suitable volume capacity sufficient to contain and isolate all soiled components of the kit 10 in question together with any fluid adhering thereto. It is contemplated that that at the end of a cleaning operation, all unused items in the kit 10 will be collected in the disposable biohazard bag 80. In certain embodiments, the disposable biohazard bag can have a capacity between about 3 gallons and about 50 gallons. It is contemplated that in certain embodiments, the biohazard bag 80 can have a capacity between 3 and 10 gallons while in others, the capacity will be between about t=8 and 20 gallons.

The disposable biohazard bag 80 can be sealable by any suitable means as by tying, banding or the like. In certain embodiments, the disposable biohazard bag 80 can be coded with suitable indicia to identify the type of disposal necessary for the material contained. It is contemplated that the identification employed on the biohazard bag 80 can coordinate with the indicia present on the other components in the kit 10.

The sealable disposable biohazard bag 80 can be located in folded relation the outer bag member 12 and can be removed as needed. The sealable disposable biohazard bag 80 can be composed of a suitable polymeric film having a thickness between 0.5 mil and 10.0 mil and can be resistant to tears and punctures. In certain embodiments, the thickness of the polymeric film can be between 2 and 5 mil.

The kit 10 can be employed to clean and sanitize a discrete treatment region in a healthcare facility by introducing the cleaning kit 10 as disclosed herein into the discrete treatment region to be cleaned. It is contemplated that each discrete treatment region to be cleaned will be assigned a specific kit 10 which will be opened once in position in the region to be cleaned.

The kit 10 can be opened by splitting the outer bag member 12 at a seam. The plurality of nonwoven wipe sheets 16 in a folded state are removed from the outer bag member 12 and transferred into a measured volume of a sanitizing solution that is sufficient to be absorbed by the plurality of nonwoven wipe sheets 16. The single-use vertical surface washing pad(s) 20 can also be transferred into contact with a suitable sanitizing solution. The sanitizing solution can be the same or different from the one employed with the non-woven wipe sheets 16 as desired or required. Similarly, the single floor pad(s) 40 can be transferred into contact with a sanitizing solution—the same or different from the solution employed with the other kit components.

In order to clean the desired discrete treatment region, the elements of the kit 10 will be employed in an order to accomplish the following steps: contacting surfaces of apparatus and devices present in the discrete room in the hospital using the plurality of non-woven wipe sheets having first sanitizing solution therein, contacting vertical perimeter surfaces of the discrete room in the hospital using the at least two single-use vertical surface washing pads charged with the second sanitizing solution and then contacting floor surfaces of the discrete room in order from outward in.

Once the cleaning operations are completed, all material that was originally contained in the outer bag member 12 is collected in the open biohazard bag 80 after use and, once the material is collected and region cleaned, the biohazard bag is sealed and disposed of a a medically suitable manner.

While the invention has been described in connection with certain embodiments, it is to be understood that the invention is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A cleaning kit for cleaning and sanitizing a defined region of a hospital or healthcare facility, the cleaning kit comprising:
    an outer bag member, the outer bag member composed of a polymeric film material, the outer bag member defining a sealed inner chamber,
    a plurality of non-woven wipe sheets contained in the sealed inner chamber defined in the outer bag member, each non-woven wipe sheet having at least one contact surface and at least one indicia present in the at least one contact surface, wherein each non-woven wipe sheet is dimensioned to deliver a volume of sanitizing charge solution to an accessory surface present in the defined region of a hospital to be cleaned;
    at least two single-use vertical surface washing pads contained in the sealed inner chamber defined in the outer bag member, each respective single-use vertical surface washing pad having an elongated body, the elongated body having a first elongated surface and a second elongated surface opposed to the first elongated surface, wherein the first elongated surface comprises a compressible microfiber region and wherein the second elongated surface has loop pile surface region configured to releasably contact a wand member and at least one scrubbing member projecting from the compressible microfiber region, each single-use vertical surface washing pad having at least one indicia the indicia having an identifier color associated therewith, wherein the wand member is external to the cleaning kit;
    at least two single-use floor pads contained in the sealed inner chamber of the outer bag member, each respective single-use floor pad having a first elongated floor pad surface and a second elongated floor pad surface, wherein the first elongated floor pad surface comprises a compressible microfiber region and wherein the second elongated floor pad surface has a loop pile surface region configured to releasably contact a single-use floor pad mounting tool and at least one scrubbing member projecting from the compressible microfiber region, wherein each single-use floor pad has at least one identifier indicia associated therewith, wherein the single-use floor pad mounting tool is external to the cleaning kit; and
    at least one sealable disposable biohazard bag located in the sealed inner chamber in the outer bag member, the at least one sealable disposable biohazard bag composed of a polymeric film.

2. The kit of claim 1 wherein the outer bag member is composed of two sheets of polymeric film, the two sheets each having outer edges, the outer edges bonded to one another in fused relationship to define the sealed inner chamber, wherein the outer bag member has a leading edge and at least one opening mechanism proximate to the leading edge.

3. The kit of claim 1 wherein the plurality of non-woven wipe sheets contained in the sealed inner chamber of the outer bag member are each individually folded and maintained in stacked and bundled relationship in the sealed inner chamber relative to one another.

4. The kit of claim 3 wherein the non-woven wipe sheets contain semi-synthetic fibers and one or more synthetic fibers, wherein the one or more synthetic fibers are present in a ratio between about 1 to 3 and 3 to 1 synthetic fibers to semi-synthetic fibers respectively.

5. The kit of claim 1 wherein the at least one indicia present on the contact surface of the non-woven wipe sheets is color-coded.

6. The kit of claim 1 wherein the single-use vertical surface washing pad contained in the sealed inner chamber defined in the outer bag member comprises:
    the elongated body, the elongated body having the first elongated surface and the second elongated surface opposed to the first elongated surface, the elongated body further having opposed major outer edges and opposed minor outer edges;
    at least one agitator strip connected to the first elongated surface of the elongated body and projecting outward therefrom, the at least one agitator strip oriented proximate to one of the outer edges; and
    wherein the at least one colored indicia is associated with either the agitator strip or the elongated body.

7. The kit of claim 6 wherein the color indicia is the agitator strip.

8. The kit of claim 6 wherein the at least two single-use vertical surface washing pad are in overlying relationship with one another at a location in the sealed inner chamber defined in the outer bag member and are proximate to the plurality of non-woven wipe sheets, wherein the agitator strip of one single use vertical surface washing pad is in releasable engagement with an outermost non-woven wipe sheet of a non-woven wipe sheet bundle and wherein the second opposed elongated surface of the one single use vertical surface washing pad is in releasable contact with the agitator strip of a second single-use vertical surface washing pad.

9. The kit of claim 1 further comprising at least one single-use mop head bundle, the mop head bundle having a plurality of elongated strip members and a headband, wherein the plurality of elongated strip members of the at least one single-use mop head bundle are connected to the headband as parallel pleated members.

10. The kit of claim 9 wherein the at least one single-use mop head bundle further comprises at least one tail band member bound to the plurality of elongate strip members at a location removed from the headband.

11. A method for cleaning and sanitizing a discrete treatment region in a healthcare facility, the method comprising the steps of:
    introducing the cleaning kit of claim 1 into the discrete treatment region of the healthcare facility to be cleaned;
    once introduced into the discrete treatment region, opening the sealed inner chamber of the outer bag member;
    transferring the plurality of nonwoven wipe sheets from the outer bag member to a measured volume of a first sanitizing solution, the measured volume of the first sanitizing solution sufficient to be absorbed by the plurality of nonwoven wipe sheets;

transferring the at least two single-use vertical surface washing pads from the outer bag member to a measured volume of a second sanitizing solution, the measured volume of the second sanitizing solution sufficient to be absorbed by the at least two single-use vertical surface washing pads;

transferring at least one of the least two single-use floor pads from the outer bag member to a measured volume of a third sanitizing solution, the measured volume of the third sanitizing solution sufficient to be absorbed by the at least two single-use vertical surface washing pads;

removing the at least one sealable disposable biohazard bags from the outer bag member and opening the biohazard disposal bag;

in order, contacting surfaces of apparatus and devices present in the discrete treatment region in the healthcare facility using the plurality of non-woven wipe sheets having the first sanitizing solution absorbed therein, contacting vertical perimeter surfaces of the discrete region in the healthcare facility using the at least two single-use vertical surface washing pads charged with the second sanitizing solution and then contacting floor surfaces of the discrete region in order from outward in; and then after use, placing all of the plurality of non-woven wipe sheets that contacted the first sanitizing solution, the at least two single-use vertical surface washing pads in the open biohazard disposal bag after use and sealing the biohazard bag.

12. The method of claim 11 wherein the kit further comprises at least one single-use mop head bundle contained in the sealed inner chamber defined in the outer bag member, the at least one mop head bundle having a plurality of elongated strip members and a headband, the elongated strip members connected to the headband and projecting outward therefrom in spaced parallel relationship to one another, the headband configured to releasably contact a mop connecter member, wherein the at least one single-use mop head bundle has at least one identifier indicia having an identifier color, and wherein the method further comprises the steps of:

contacting the at least one single-use mop head bundle with a floor sanitizing solution;

using the at least one single-use mop head bundle with a floor sanitizing solution to contact floor surfaces in the discrete region of the healthcare facility; and then placing the at least one single-use mop head bundle in the open biohazard disposal bag after use and sealing the biohazard bag.

13. The kit of claim 1 wherein the at least one sealable disposable biohazard bag located in the sealed inner chamber in the outer bag member is in a folded configuration and wherein the polymeric film has a thickness between 0.5 mil and 10.0 mil.

14. The kit of claim 1 further comprising at least one single-use mop head bundle contained in the sealed inner chamber defined in the outer bag member, the at least one mop head bundle having a plurality of elongated strip members and a headband, the elongated strip members connected to the headband and projecting outward therefrom in spaced parallel relationship to one another, the headband configured to releasably contact a mop connecter member, wherein the at least one single-use mop head bundle has at least one identifier indicia having the identifier color.

15. The kit of claim 14 wherein the plurality of elongated parallel strip members are each composed of non-woven fabric material.

16. A cleaning kit for cleaning and sanitizing a defined region of a hospital or healthcare facility, the cleaning kit comprising:

an outer bag member, the outer bag member composed of a polymeric film material, the outer bag member defining a sealed inner chamber, a plurality of non-woven wipe sheets contained in the sealed inner chamber defined in the outer bag member, each non-woven wipe sheet having at least one contact surface and at least one indicia present in the at least one contact surface, wherein each non-woven wipe sheet is dimensioned to deliver a volume of sanitizing charge solution to an accessory surface present in the defined region of a hospital to be cleaned;

at least two single-use vertical surface washing pads contained in the sealed inner chamber defined in the outer bag member, each respective single-use vertical surface washing pad having an elongated body, the elongated body having a first elongated surface and a second elongated surface opposed to the first elongated surface, wherein the first elongated surface comprises a compressible microfiber region and wherein the second elongated surface has loop pile surface region configured to releasably contact a wand member and at least one scrubbing member projecting from the compressible microfiber region, each single-use vertical surface washing pad having at least one indicia the indicia having an identifier color associated therewith, wherein the wand member is external to the cleaning kit;

at least two single-use floor pads contained in the sealed inner chamber of the outer bag, each respective single-use floor pad having a first elongated floor pad surface and a second elongated floor pad surface, wherein the first elongated floor pad surface comprises a compressible microfiber region and wherein the second elongated floor pad surface has a loop pile surface region configured to releasably contact a single-use floor pad mounting tool and at least one scrubbing member projecting from the compressible microfiber region, wherein each single-use floor pad has at least one identifier indicia associated therewith, wherein the single-use floor pad mounting tool is external to the cleaning kit;

at least one sealable disposable biohazard bag located in the sealed inner chamber in the outer bag member, the at least one sealable disposable biohazard bag composed of a polymeric film having a thickness between 0.5 mil and 10.0 mil; and optionally, at least one single-use mop head bundle contained in the sealed inner chamber of the outer bag member, the mop head bundle having a plurality of elongated strip members and a headband, the elongated strip members connected to the headband and projecting outward therefrom in spaced parallel relationship to one another, the parallel elongated strip members composed of non-woven fabric material, the non-woven strip members connected to a headband, the headband configured to releasably contact a mop connecter member, wherein the mop head bundle has at least one identifier indicia.

17. The kit of claim 16 wherein the single-use vertical surface washing pad contained in the sealed inner chamber defined in the outer bag member comprises:

the elongated body, the elongated body having the first elongated surface and the second elongated surface opposed to the first elongated surface, the elongated body further having opposed major outer edges and opposed minor outer edges;

at least one agitator strip connected to the first elongated surface of the elongated body and projecting outward therefrom, the at least one agitator strip oriented proximate to one of the outer edges; and wherein the at least one colored indicia is associated with either the agitator strip or the elongated body.

18. The kit of claim 17 further comprising at least one single-use mop head bundle contained in the sealed inner chamber defined in the outer bag member, the at least one mop head bundle having a plurality of elongated strip members and a headband, the elongated strip members connected to the headband and projecting outward therefrom in spaced parallel relationship to one another, the headband configured to releasably contact a mop connecter member, wherein the at least one single-use mop head bundle has at least one identifier indicia having the identifier color.

\* \* \* \* \*